US009585382B2

(12) United States Patent
Klingelhoefer et al.

(10) Patent No.: US 9,585,382 B2
(45) Date of Patent: Mar. 7, 2017

(54) COMPOSITION COMPRISING A PESTICIDE AND AN ACETAL SOLVENT

(75) Inventors: Paul Klingelhoefer, Mannheim (DE); Gerhard Schnabel, Elsenfeld (DE); Ralf Pelzer, Fuerstenberg (DE); Wolfgang Spiegler, Worms (DE)

(73) Assignee: BASF SE, Ludwigshafen (DE)

( * ) Notice: Subject to any disclaimer, the term of this patent is extended or adjusted under 35 U.S.C. 154(b) by 783 days.

(21) Appl. No.: 13/457,789

(22) Filed: Apr. 27, 2012

(65) Prior Publication Data

US 2012/0277101 A1    Nov. 1, 2012

Related U.S. Application Data

(60) Provisional application No. 61/480,394, filed on Apr. 29, 2011.

(30) Foreign Application Priority Data

May 17, 2011    (EP) .................................. 11166304

(51) Int. Cl.
| | | |
|---|---|---|
| *A01N 25/02* | (2006.01) | |
| *A01N 43/40* | (2006.01) | |
| *A01N 43/42* | (2006.01) | |
| *A01N 43/84* | (2006.01) | |
| *A01N 47/24* | (2006.01) | |
| *A01N 31/16* | (2006.01) | |

(52) U.S. Cl.
CPC ............ *A01N 25/02* (2013.01); *A01N 31/16* (2013.01); *A01N 43/40* (2013.01); *A01N 43/42* (2013.01); *A01N 43/84* (2013.01); *A01N 47/24* (2013.01)

(58) Field of Classification Search
CPC ........ A01N 25/02; A01N 43/40; A01N 43/42; A01N 43/84; A01N 47/24; A01N 2300/00; A01N 31/16
See application file for complete search history.

(56) References Cited

U.S. PATENT DOCUMENTS

| | | | | |
|---|---|---|---|---|
| 2,075,359 A | * | 3/1937 | Euclid et al. ................... | 514/63 |
| 3,826,822 A | | 7/1974 | Moulin et al. | |
| 4,791,127 A | * | 12/1988 | Kato et al. ..................... | 514/369 |
| 5,116,402 A | * | 5/1992 | Dutka ................... | A01N 25/32 |
| | | | | 504/100 |
| 5,626,852 A | | 5/1997 | Suffis et al. | |

FOREIGN PATENT DOCUMENTS

| | | | |
|---|---|---|---|
| DE | 2 200617 | | 7/1972 |
| EP | 0 230 773 | | 8/1987 |
| JP | 52110823 A | * | 9/1977 |
| JP | 2002068905 A | * | 3/2002 |
| WO | WO 97/34986 | | 9/1997 |
| WO | WO 01/17345 | | 3/2001 |

OTHER PUBLICATIONS

Sigma Aldrich, Safety Data Sheet, S-Ethyl-N,N-dipropylthiocarbamate, Jan. 17, 2015.*
International Search Report completed Jul. 3, 2012, in International Application No. PCT/EP2012/057575.

* cited by examiner

*Primary Examiner* — John Pak
*Assistant Examiner* — Nathan W Schlientz
(74) *Attorney, Agent, or Firm* — Brinks Gilson & Lione

(57) ABSTRACT

The present invention relates to an agrochemical composition comprising a pesticide and a solvent of the formula (B) as described hereinbelow. The invention furthermore relates to a process for the preparation of the composition by bringing the pesticide and the solvent into contact; a use of the solvent of the formula (B) as a solvent for pesticides; methods for controlling phytopathogenic fungi and/or undesired vegetation and/or undesired insect or mite attack and/or for regulating the growth of plants, wherein the composition is allowed to act on the respective pests, their environment or on the plants to be protected from the respective pest, on the soil and/or on undesired plants and/or on the crop plants and/or on their environment; and on seed comprising the composition.

9 Claims, No Drawings

COMPOSITION COMPRISING A PESTICIDE AND AN ACETAL SOLVENT

This application claims the benefit of U.S. Provisional Application No. 61/480,394 filed Apr. 29, 2011, the entire contents of which are hereby incorporated herein by reference. This application also claims priority under 35 U.S.C. §119 to European Patent Application No. 11166304.3 filed May 17, 2011 the entire contents of which is hereby incorporated herein by reference.

The present invention relates to an agrochemical composition comprising a pesticide and a solvent of the formula (B) as described hereinbelow. The invention furthermore relates to a process for the preparation of the composition by bringing the pesticide and the solvent into contact; a use of the solvent of the formula (B) as a solvent for pesticides; methods for controlling phytopathogenic fungi and/or undesired vegetation and/or undesired insect or mite attack and/or for regulating the growth of plants, wherein the composition is allowed to act on the respective pests, their environment or on the plants to be protected from the respective pest, on the soil and/or on undesired plants and/or on the crop plants and/or on their environment; and to seed comprising the composition. Combinations of preferred features with other preferred features are comprised by the present invention.

WO2001/17345 discloses a composition comprising a biologically active compound and an acetal solvent.

A disadvantage of the known agrochemical compositions comprising acetals is, inter alia, that it is impossible to dissolve a high pesticide concentration. Another disadvantage is that acetals are odoriferous, have a low flash point, high viscosity, high toxicity and high solubility in water. An object of the present invention was to provide a composition comprising pesticide, which composition overcomes these disadvantages.

The object was achieved by a composition, in particular an agrochemical composition, comprising a pesticide and a solvent of the formula (B)

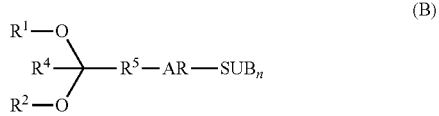

(B)

wherein
$R^1$ and $R^2$ independently of one another are $C_1$-$C_{20}$-alkyl or together are a $C_2$-$C_{14}$-alkylene,
$R^4$ is hydrogen, $C_1$-$C_{20}$-alkyl, $C_1$-$C_{30}$-aryl, $C_1$-$C_{30}$-alkylaryl or $C_1$-$C_{30}$-aralkyl, it being possible for the C atoms optionally to be substituted by hetero-atom-comprising groups,
$R^5$ is a single bond or $C_1$-$C_6$-alkylene which can optionally be substituted by heteroatom-comprising groups and/or which has hetero atoms incorporated in the $C_1$-$C_6$-alkylene chain,
AR is an aromatic group,
SUB independently of one another is a hetero-atom-comprising group, and
n is a value of from 1 to 5.

$R^1$ and $R^2$ independently of one another can be $C_1$-$C_{20}$-alkyl, it being possible for the alkyl radical to be linear or branched. It is preferably linear. Usually, $R^1$ and $R^2$ are aliphatic. Usually, $R^1$ and $R^2$ are unsubstituted. Preferably, $R^1$ and $R^2$ are identical. $R^1$ and $R^2$ are preferably independently of one another $C_1$-$C_{12}$-alkyl, especially preferably $C_1$-$C_8$-alkyl, specifically preferably $C_1$-$C_4$-alkyl (such as methyl, ethyl, n-propyl, iso-propyl, n-butyl, iso-butyl). In particular, $R^1$ and $R^2$ are both methyl, ethyl or n-propyl, above all methyl or ethyl, specifically methyl.

$R^1$ and $R^2$ can together be a $C_2$-$C_{14}$-alkylene. In this case, $R^1$ and $R^2$ would form a cyclic acetal group. Usually, the $C_2$-$C_{14}$-alkylene is aliphatic. Usually the $C_2$-$C_{14}$-alkylene is unsubstituted. Preferably, $R^1$ and $R^2$ together are a $C_2$-$C_8$-alkylene, especially preferably a $C_2$-$C_4$-alkylene, and specifically ethylene, n-propylene or isopropylene.

$R^4$ is preferably hydrogen, $C_1$-$C_{20}$-alkyl, $C_1$-$C_{30}$-alkylaryl or $C_1$-$C_{30}$-aralkyl, it being possible for the C atoms optionally to be substituted by at least one $C_1$-$C_{20}$-alkoxy group. $R^4$ is especially preferably hydrogen or $C_1$-$C_{12}$-alkyl, in particular hydrogen or methyl and very specifically hydrogen.

$R^5$ is preferably a single bond or $C_1$-$C_6$-alkylene, especially preferably a single bond.

AR is an aromatic group which has n substituents SUB. AR is preferably a phenyl or naphthyl group which has n substituents SUB. AR is especially preferably a phenyl group with n=1 to 3 substituents SUB, where n is in particular 1.

SUB independently of one another is at least one organic group, where n indicates the number of these groups per AR unit. Examples of SUB are organic groups comprising halide, carboxylic ester, alkoxylate, carboxamides, alkyl, aryl, alkylaryl, aralkyl, cyanide, nitrate, ketones, sulfate, sulfonate, phosphate, phosphonate.

Preferably, SUB is at least one $C_1$-$C_{20}$-alkoxy group, in particular —O—$R^3$. $R^3$ can be $C_1$-$C_{20}$-alkyl, it being possible for the alkyl radical to be linear or branched. It is preferably linear. Usually, $R^3$ is aliphatic. Usually, $R^3$ is unsubstituted. $R^3$ is preferably $C_1$-$C_{12}$-alkyl, especially preferably $C_1$-$C_8$-alkyl, specifically preferably $C_1$-$C_4$-alkyl (such as methyl, ethyl, n-propyl, iso-propyl, n-butyl, iso-butyl). In particular, $R^3$ is methyl.

In a further preferred form, SUB is at least one (preferably precisely one) alkyl group. The alkyl group is preferably a $C_1$-$C_{20}$-alkyl group, especially preferably a $C_1$-$C_{12}$-alkyl group and specifically a $C_1$-$C_6$-alkyl group, such as methyl or tert-butyl. Examples of solvents of the formula (B) where SUB is an alkyl group are the following structures (B1) and (B2):

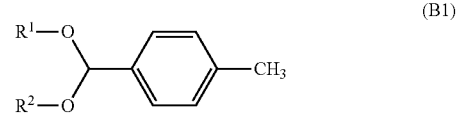

(B1)

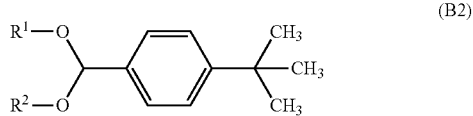

(B2)

Specially suitable structures (B1) and (B2) are those in which both $R^1$ and $R^2$ are methyl. The substituent(s) SUB can be present on the aromatic ring AR in various constitutions, such as in the ortho, meta or para constitution. It is preferably present in the para constitution.

The index n preferably has a value of from 1 to 3, especially preferably a value of 1 or 2, and in particular 1.

In a preferred form, $R^5$ is a single bond, AR is a phenyl or naphthyl group and n is a value of 1 or 2. In an especially preferred form, $R^5$ is a single bond, AR is a phenyl or naphthyl group, n has a value of 1 or 2, SUB is —O—$R^3$ and $R^4$ is hydrogen or methyl.

Suitable examples of solvents of the formula (B) or of the formula (A) are the following structures (1) to (15):

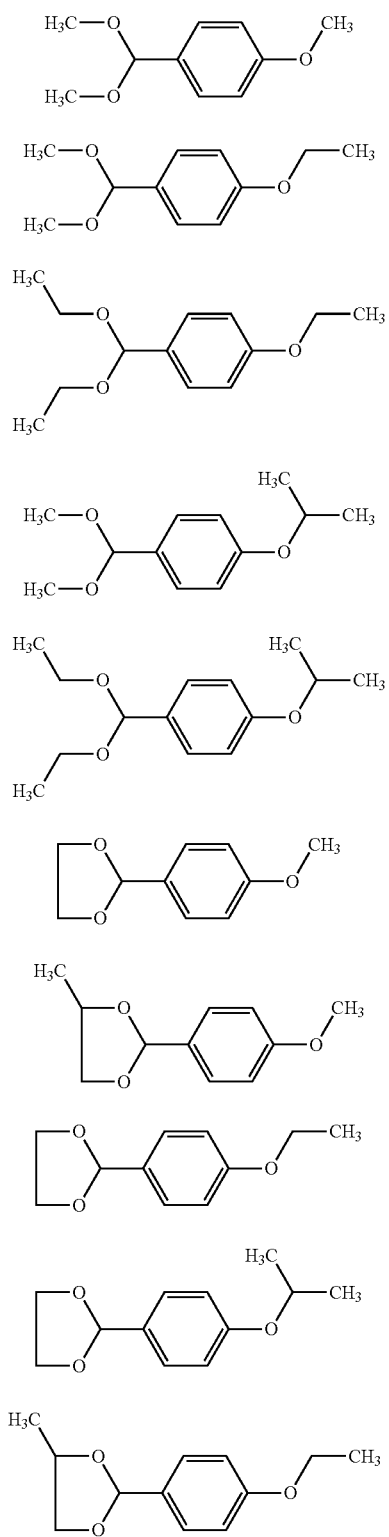

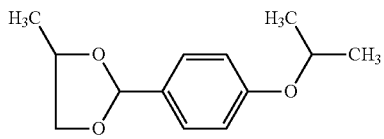

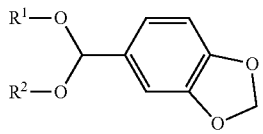

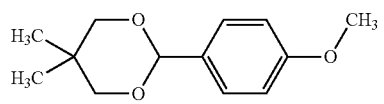

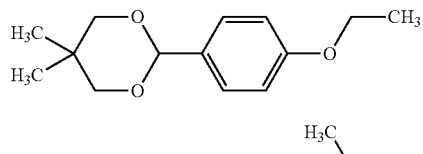

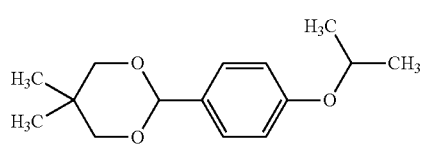

Specifically suitable structures (12) are those in which both $R^1$ and $R^2$ are methyl.

In a specifically preferred embodiment, the solvent is a solvent of the formula (A)

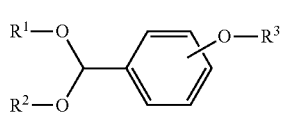

(A)

where $R^1$ and $R^2$ independently of one another are $C_1$-$C_{20}$-alkyl or together are a $C_2$-$C_{14}$-alkylene, and $R^3$ is $C_1$-$C_{20}$-alkyl.

In formula (A), $R^1$ and $R^2$ independently of one another may be $C_1$-$C_{20}$-alkyl, it being possible for the alkyl radical to be linear or branched. Preferably, it is linear. Usually, $R^1$ and $R^2$ are aliphatic. Usually, $R^1$ and $R^2$ are unsubstituted. Preferably, $R^1$ and $R^2$ are identical. Preferably, $R^1$ and $R^2$ independently of one another are $C_1$-$C_{12}$-alkyl, particularly preferably $C_1$-$C_8$-alkyl, especially preferably $C_1$-$C_4$-alkyl (such as methyl, ethyl, n-propyl, iso-propyl, n-butyl, iso-butyl). In particular, both $R^1$ and $R^2$ are methyl, ethyl or n-propyl, above all methyl or ethyl, specifically methyl.

In formula (A), $R^1$ and $R^2$ together may be a $C_2$-$C_{14}$-alkylene. In this case, $R^1$ and $R^2$ would form a cyclic acetal group. Usually, the $C_2$-$C_{14}$-alkylene is aliphatic. Usually, the $C_2$-$C_{14}$-alkylene is linear or branched. Usually, the $C_2$-$C_{14}$-alkylene is free from heteroatom-comprising substituents. Preferably, $R^1$ and $R^2$ together are a $C_2$-$C_8$-alkylene, especially preferably a $C_2$-$C_5$-alkylene, specifically ethylene, n-propylene, iso-propylene (such as —$CH_2$—$CH(CH_3)$—), iso-butylene (such as —$CH_2$—$CH(CH_3)_2$—) or iso-pentylene (such as —$CH_2$—$C(CH_3)_2$—$CH_2$—), and very specifically ethylene, n-propylene or iso-propylene (such as —$CH_2$—$CH(CH_3)$—).

In formula (A) $R^3$ may be $C_1$-$C_{20}$-alkyl, it being possible for the alkyl radical to be linear or branched. Preferably, it is linear. Usually, $R^3$ is aliphatic. Usually, $R^3$ is unsubstituted. Preferably, $R^3$ is $C_1$-$C_{12}$-alkyl, particularly preferably $C_1$-$C_8$-alkyl, especially preferably $C_1$-$C_4$-alkyl (such as methyl, ethyl, n-propyl, iso-propyl, n-butyl, iso-butyl). In particular, $R^3$ is methyl.

The solvent of the formula (A) can be present in the ortho, meta or para constitution. It is preferably present in the para constitution.

In formula (A), $R^1$ and $R^2$ independently of one another are preferably $C_1$-$C_4$-alkyl or, together, a $C_2$-$C_6$-alkylene, and $R^3$ is $C_1$-$C_4$-alkyl. Especially preferably, $R^1$, $R^2$ and $R^3$ are methyl.

Specifically suitable solvents of the formula (A) are those of the formulae A1, A2 or A3, with the formula A1 being most preferred.

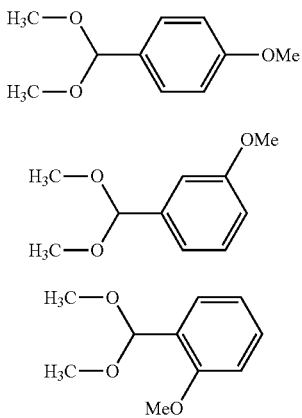

The solvent of the formula (B) (in particular of the formula (A)) usually has a solubility in water at 20° C. of no more than 1.0% by weight, preferably of no more than 0.5% by weight, especially preferably of no more than 0.1% by weight.

The compounds of the formula (B) (in particular of the formula (A)) are generally known and commercially available, for example p-anisaldehyde dimethyl acetal. The acetals of the formula (B) (in particular of the formula (A)) can be prepared by customary processes, for example by reacting an alkoxy-substituted benzaldehyde with an alcohol.

The composition according to the invention usually comprises at least 10% by weight, preferably at least 20% by weight, especially preferably at least 30% by weight of solvent of the formula (B) (in particular of the formula (A)) based on the composition. In most cases, the composition comprises no more than 95% by weight, preferably no more than 90% by weight, especially preferably no more than 80% by weight, of solvent of the formula (B) (in particular of the formula (A)).

The solvent of the formula (B) (in particular of the formula (A)) usually comprises the pesticide, which, in this context, may be present in solid, dissolved, suspended and/or emulsified form. Preferably, the solvent of the formula (B) (in particular of the formula (A)) comprises the pesticide in dissolved form.

An agrochemical composition is usually understood as meaning a composition which comprises a pesticide and which can be employed in a method of controlling phytopathogenic fungi and/or undesired plant growth and/or undesired insect or mite attack and/or for regulating the growth of plants, where the composition is allowed to act on the respective pests, their environment or on the plants to be protected from the respective pest, on the soil and/or on undesired plants and/or on the useful plants and/or their environment.

The expression pesticide refers to at least one active substance selected from the group consisting of the fungicides, insecticides, nematicides, herbicides, safeners and/or growth regulators. Preferred pesticides are fungicides, insecticides and herbicides, in particular fungicides and herbicides. Mixtures of pesticides of two or more of the above-mentioned classes may also be used. The skilled worker is familiar with such pesticides, which can be found, for example, in Pesticide Manual, 14th Ed. (2006), The British Crop Protection Council, London.

Suitable insecticides are insecticides from the class of the carbamates, organophosphates, organochlorine insecticides, phenylpyrazoles, pyrethroids, neonicotinoids, spinosins, avermectins, milbemycins, juvenile hormone analogs, alkyl halides, organotin compounds, nereistoxin analogs, benzoylureas, diacyihydrazines, METI acaricides, and insecticides such as chloropicrin, pymetrozine, flonicamid, clofentezine, hexythiazox, etoxazole, diafenthiuron, propargite, tetradifon, chlorfenapyr, DNOC, buprofezin, cyromazine, amitraz, hydramethylnon, acequinocyl, fluacrypyrim, rotenon, or their derivatives. Suitable fungicides are fungicides from the classes dinitroanilines, allylamines, anilinopyrimidines, antibiotics, aromatic hydrocarbons, benzenesulfonamides, benzimidazoles, benzoisothiazoles, benzophenones, benzothiadiazoles, benzotriazines, benzylcarbamates, carbamates, carboxamides, carboxylic acid amides, chloronitriles, cyanoacetamide oximes, cyanoimidazoles, cyclopropanecarboxamides, dicarboximides, dihydrodioxazines, dinitrophenyl crotonates, dithiocarbamates, dithiolanes, ethylphosphonates, ethylaminothiazolecarboxamides, guanidines, hydroxy(2-amino)pyrimidines, hydroxyanilides, imidazoles, imidazolinones, inorganic substances, isobenzofuranones, methoxyacrylates, methoxycarbamates, morpholines, N-phenylcarbamates, oxazolidinediones, oximinoacetates, oximinoacetamides, peptidylpyrimidine nucleosides, phenylacetamides, phenylamides, phenylpyrroles, phenylureas, phosphonates, phosphoro-thiolates, phthalamic acids, phthalimides, piperazines, piperidines, propionamides, pyridazinones, pyridines, pyridinylmethylbenzamides, pyrimidinamines, pyrimidines, pyrimidinonehydrazones, pyrroloquinolinones, quinazolinones, quinolines, quinones, sulfamides, sulfamoyltriazoles, thiazolecarboxamides, thiocarbamates, thiophanate, thiophene-carboxamides, toluamides, triphenyltin compounds, triazines, triazoles. Suitable herbicides are herbicides from the classes of acetamides, amides, aryloxyphenoxypropionates, benzamides, benzofuran, benzoic acids, benzothiadiazinones, bipyridylium, carbamates, chloroacetamides, chlorocarboxylic acids, cyclohexanediones, dinitroanilines, dinitrophenol, diphenyl ethers, glycines, imidazolinones, isoxazoles, isoxazolidinones, nitriles, N-phenylphthalimides, oxadiazoles, oxazolidinediones, oxyacetamides, phenoxycarboxylic acids, phenylcarbamates, phenylpyrazoles, phenylpyrazolines, phenylpyridazines, phosphinic acids, phosphoroamidates, phosphorodithioates, phthalamates, pyrazoles, pyridazinones, pyridines, pyridinecarboxylic acids, pyridinecarboxamides, pyrimidinediones, pyrimidinyl(thio)benzoates, quinolinecarboxylic acids, sem icarbazones, sulfonylaminocarbonyltriazolinones, sulfonylureas, tetrazolinones, thiadiazoles, thiocarbamates, triazines, triazinones, triazoles, triazolinones, triazolocarboxam ides, triazolopyrimidines, triketones, uracils, ureas.

The pesticide is usually soluble at 20° C. in the solvent of the formula (B) (in particular of the formula (A)) to at least 10 g/l, preferably to at least 30 g/l and especially preferably to at least 50 g/l.

The pesticide is usually soluble in water at 20° C. to no more than 10 g/l, preferably to no more than 1 g/l and especially preferably to no more than 0.1 g/l.

The composition according to the invention can also comprise further pesticides. The further pesticides can be present in dissolved, suspended and/or emulsified form.

In a further embodiment, the pesticide is present in the liquid agrochemical composition in dissolved form. Preferably, the pesticide is dissolved in the solvent system at 20° C. to at least 90% by weight, preferably to at least 98% by weight, based on the pesticide.

In a further embodiment, at least one pesticide is suspended to at least 90% by weight, based on the pesticide, in the solvent system in the form of solid particles. If the composition comprises at least two pesticides, at least one pesticide is dissolved to at least 90% by weight in the solvent system. Preferably, the pesticide is suspended to at least 95% by weight, especially preferably to at least 98% by weight, in the solvent system.

The composition according to the invention usually comprises from 0.1 to 70% by weight of pesticide, preferably from 1 to 50%, in particular from 3 to 30% by weight, based on the composition.

The composition according to the invention comprises formulation auxiliaries, the choice of the auxiliaries usually depending on the specific embodiment and/or the active substance. Examples of suitable formulation auxiliaries are additional solvents, surfactants and other surface-active substances (such as solubilizers, protective colloids, wetting agents and adhesives), adjuvants, organic and inorganic thickeners, bactericides, antifreeze agents, antifoams, colorants and stickers (for example for the treatment of seeds).

Suitable additional solvents which may be present in the composition in addition to the solvent of the formula (B) are organic solvents such as mineral oil fractions of medium to high boiling point such as kerosene and diesel oil, furthermore coal tar oils and oils of vegetable or animal origin, aliphatic, alicyclic and aromatic hydrocarbons, for example paraffins, tetrahydronaphthalene, alkylated naphthalenes and their derivatives, alkylated benzenes and their derivatives, alcohols such as ethanol, propanol, butanol, benzyl alcohol and cyclohexanol, glycols, ketones such as cyclohexanone, gamma-butyrolactone, dimethyl fatty acid amides, fatty acids and fatty acid esters, and strongly polar solvents, for example amines such as N-methylpyrrolidone. In principle, it is also possible to use solvent mixtures. It is preferred to add no more than 40% by weight, preferably no more than 20% by weight, of additional solvents to the composition according to the invention, in each case based on the composition.

Surfactants can be employed individually or as a mixture. Surfactants are compounds which reduce the surface tension of water. Suitable surfactants are anionic, cationic, nonionic and amphoteric surfactants, block polymers and polyelectrolytes. The composition according to the invention preferably comprises at least one anionic surfactant.

Suitable anionic surfactants are alkali, alkaline-earth or ammonium salts of sulfonates, sulfates, phosphates or carboxylates. Examples of sulfonates are alkylarylsulfonates, diphenylsulfonates, alpha-olefinsulfonates, lignosulfonates, sulfonates of fatty acids and oils, sulfonates of ethoxylated alkylphenols, sulfonates of ethoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates and carboxylated alcohol or alkylphenol ethoxylates. Preferred anionic surfactants are sulfonates of ethoxylated arylphenols, in particular phosphated or sulfated di- and/or tristyrylphenyl alkoxylates, as are described for example in WO 2007/110355, page 3, line 30 to page 5, line 11.

Suitable nonionic surfactants are alkoxylates, N-alkylated fatty acid amides, amine oxides, esters or sugar-based surfactants. Examples of alkoxylates are compounds such as alcohols, alkylphenols, amines, amides, arylphenols, fatty acids or fatty acid esters which have been alkoxylated. Ethylene oxide and/or propylene oxide may be employed for the alkoxylation, preferably ethylene oxide. Examples of N-alkylated fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides.

Suitable cationic surfactants are quaternary surfactants, for example quaternary ammonium compounds with one or two hydrophobic groups, or salts of long-chain primary amines. Suitable amphoteric surfactants are alkylbetaines and imidazolines. Suitable block polymers are block polymers of the A-B or A-B-A type comprising blocks of polyethylene oxide and polypropylene oxide or of the A-B-C type comprising alkanol, polyethylene oxide and polypropylene oxide. Suitable polyelectrolytes are polyacids or polybases. Examples of polyacids are alkali metal salts of polyacrylic acid. Examples of polybases are polyvinylamines or polyethyleneamines.

The composition according to the invention can comprise various amounts of surfactants. It can comprise from 0.1 to 40% by weight, preferably from 1 to 30 and in particular from 2 to 20% by weight total amount of surfactant, based on the total amount of the composition.

Examples of adjuvants are organically modified polysiloxanes such as BreakThruS 240®; alcohol alkoxylates such as Atplus®245, Atplus®MBA 1303, Plurafac®LF and Lutensol® ON; EO/PO block polymers, for example Pluronic® RPE 2035 and Genapol® B; alcohol ethoxylates, for example Lutensol® XP 80; and sodium dioctylsulfosuccinate, for example Leophen® RA.

Examples of thickeners (i.e. compounds which impart to the composition a modified flow behavior, i.e. high viscosity at rest and low viscosity in motion) are polysaccharides and organic and inorganic layer minerals such as xanthan gum (Kelzan®, CP Kelco), Rhodopol® 23 (Rhodia) or Veegum® (R.T. Vanderbilt) or Attaclay® (Engelhard Corp.).

Bactericides can be added to stabilize the composition. Examples of bactericides are those based on dichlorophen and benzyl alcohol hemiformal (Proxel® from ICI or Acticide® RS from Thor Chemie and Kathon® MK from Rohm & Haas) and on isothiazolinone derivatives, such as alkylisothiazolinones and benzisothiazolinones (Acticide® MBS from Thor Chemie).

Examples of suitable antifreeze agents are ethylene glycol, propylene glycol, urea and glycerol.

Examples of antifoams are silicone emulsions (such as, for example Silikon® SRE, Wacker, Germany or Rhodorsil®, Rhodia, France), long-chain alcohols, fatty acids, salts of fatty acids, organofluorine compounds and their mixtures.

Examples of colorants are both pigments, which are sparingly soluble in water, and dyes, which are soluble in water. Examples which may be mentioned are the dyes and pigments known by the names Rhodamin B, C. I. Pigment Red 112 and C. I. Solvent Red 1, Pigment Blue 15:4, Pigment Blue 15:3, Pigment Blue 15:2, Pigment Blue 15:1, Pigment Blue 80, Pigment Yellow 1, Pigment Yellow 13, Pigment Red 48:2, Pigment Red 48:1, Pigment Red 57:1, Pigment Red 53:1, Pigment Orange 43, Pigment Orange 34, Pigment Orange 5, Pigment Green 36, Pigment Green 7, Pigment White 6, Pigment Brown 25, Basic Violet 10, Basic Violet 49, Acid Red 51, Acid Red 52, Acid Red 14, Acid Blue 9, Acid Yellow 23, Basic Red 10, Basic Red 108.

Examples of stickers are polyvinylpyrrolidone, polyvinyl acetate, polyvinyl alcohol and cellulose ethers (Tylose®, Shin-Etsu, Japan).

The compositions according to the invention are usually present in the form of agrochemical formulations. Suitable agrochemical formulations are water-soluble concentrates (SL, LS), redispersible concentrates (DC), emulsifiable concentrates (EC), emulsions (EW, EO, ES, ME), suspensions (SC, OD, FS), suspoemulsions (SE), and powders and granules (WP, WG).

Preferably, the composition is present in the form of an emulsifiable concentrate, of an emulsion, a suspension (such as OD, FS), a suspoemulsion, a powder or granules. In a further preferred embodiment, the composition is present in the form of a WG formulation, such as described, for example, in WO2007/028505 or WO2007/028504.

In most cases, the composition according to the invention will be diluted prior to application in order to prepare the so-called tank mix. Substances which are suitable for dilution are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, strongly polar solvents, for example dimethyl sulfoxide, N-methylpyrrolidone or water. It is preferred to use water. The dilute composition is usually applied by spraying or fogging. Oils of various types, wetters, adjuvants, herbicides, bactericides, fungicides may be added to the tank mix immediately prior to application (tank mix). These agents can be admixed to the compositions according to the invention in a weight ratio from 1:100 to 100:1, preferably 1:10 to 10:1. The pesticide concentration in the tank mix can be varied within substantial ranges. In general, they are between 0.0001 and 10%, preferably between 0.01 and 1%. When used in plant protection, the application rates are between 0.01 and 2.0 kg of active substance per ha, depending on the nature of the desired effect.

The present invention also relates to the use of a composition according to the invention for controlling phytopathogenic fungi and/or undesired plant growth and/or undesired insect or mite attack and/or for regulating the growth of plants, where the composition is allowed to act on the respective pests, their environment or the plants to be protected from the respective pest, the soil and/or on undesired plants and/or the useful plants and/or their environment. The invention furthermore relates to the use of a composition according to the invention for controlling undesired insect or mite attack on plants and/or for controlling phytopathogenic fungi and/or for controlling undesired plant growth, where seeds of useful plants are treated with the composition.

Furthermore, the invention relates to seed which has been treated with a composition according to the invention. Preferably, the seed has been dressed with the composition according to the invention. Dressing means that the seed has been treated with the composition and the composition remains on the seed. This composition can be applied to the seed in undiluted or, preferably, diluted form. Here, the composition in question can be diluted 2- to 10-fold, so that from 0.01 to 60% by weight, preferably from 0.1 to 40% by weight, of pesticide are present in the compositions to be used for dressing the seed. The application can take place before sowing. The treatment of plant propagation material, in particular the treatment of seed, is known to the skilled worker and is carried out by dusting, coating, pelleting, dipping or soaking the plant propagation material, the treatment preferably being effected by pelleting, coating and dusting, so that, for example, premature germination of the seed is prevented. In the treatment of seed, one will generally use pesticide amounts of from 1 to 1000 g/100 kg, preferably from 5 to 100 g/100 kg propagation material or seed.

The invention furthermore relates to a process for the preparation of a composition according to the invention, where the pesticide and the solvent of the formula (B) (in particular of the formula (A)) are brought into contact, for example mixed. Preferred solvents of the formula (B) and solvent are as described hereinabove. Mixing is carried out by customary mixing processes, such as stirring, shaking or any other energy input. Further adjuvants which are employed for the preparation of agrochemical formulations can be added in customary amounts. Examples of suitable formulation auxiliaries are as described above.

The present invention also relates to the use of the solvent of the formula (B) as a solvent for pesticides, for example in agrochemical formulations. Preferred solvents of the formula (B) are as described hereinabove. Agrochemical formulations are known to the skilled worker. They usually comprise a pesticide and, optionally, adjuvants for agrochemical formulations, for example the abovementioned adjuvants for agrochemical formulations.

The present invention also relates to the use of the solvent of the formula (B) in agrochemical compositions, for example as formulation auxiliaries, for example the abovementioned adjuvants for agrochemical formulations.

Advantages of the present invention are, inter alia, that a high concentration of pesticide can be dissolved in the solvent of the formula (B) (in particular of the formula (A)). The solvent of the formula (B) (in particular of the formula (A)) can be prepared on an industrial scale in a simple and inexpensive manner, starting with known materials. Anisaldehyde dimethyl acetal, in particular, is available on a large industrial scale. A further advantage of the solvents of the formula (B) (in particular of the formula (A)) is that they are very low in odor; that their flash point is very high; their low viscosity; their low toxicity and their low solubility in water. These advantages are very important so that the solvents of the formula (B) (in particular of the formula (A)) can be employed safely by farmers, whereby advantageous agrochemical formulations can be provided.

The examples which follow illustrate the invention without imposing any limitation.

EXAMPLES

Benzaldehyde dimethyl acetal (not inventive): commercially available from Acros Organics, >98% by weight, CAS No. 1125-88-8.

p-Anisaldehyde dimethyl acetal (4-methoxybenzaldehyde dimethyl acetal): commercially available from Acros Organics, >98% by weight, CAS No. 2186-92-7.

Example 1

Solubility of Pesticides

A) Pyraclostrobin was added at 20° C. to benzaldehyde dimethyl acetal or p-anisaldehyde dimethyl acetal, with stirring. In both cases, a pyraclostrobin solubility of at least 50% by weight was observed.

B) Clodinafop-propargyl and cloquintocet-mexyl (weight ratio 4:1) were added at 20° C. to benzaldehyde dimethyl acetal or to p-anisaldehyde dimethyl acetal with stirring. In both cases, it was possible to prepare a solution with a strength of at least 50% by weight.

C) The maximum solubility of the herbicide 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinan-2,4-dione was determined at 20° C., and 63 g/l were found in Solvesso® 200 ND (an aromatic solvent mixture with >99% by weight of aromatics; boiling range 235-290° C.), 19 g/l in Solvesso® 150 ND (an aromatic solvent mixture with >99% by weight aromatics; boiling range 179-194° C.) and 214 g/l in p-anisaldehyde dimethyl acetal.

Example 2

Solubility in Water

The solubility of benzaldehyde dimethyl acetal or p-anisaldehyde dimethyl acetal in water at 20° C. was analyzed. In both cases, it was not possible to dissolve more than 0.1% by weight in water.

Example 3

Odor

In a blind test involving three persons, the odor of benzaldehyde dimethyl acetal or p-anisaldehyde dimethyl acetal was compared.

Benzaldehyde dimethyl acetal had a pungent odor. The safety data sheet described the odor as "strong note, metallic, almond".

p-Anisaldehyde dimethyl acetal had a mild odor. The safety data sheet from Acros Organics (last updated on Jul. 20, 2009), the odor was described as a "pleasant odor" or "floral" (in the safety data sheet from TCI Europe NV, last updated on Dec. 22, 2010).

Example 4

Toxicity

According to the European Union as specified in EU directive 67/548/EEC, 1999/45/EC or 88/379/EEC, benzaldehyde dimethyl acetal was classified as "Xn—harmful" and "R22—harmful if swallowed". In comparison, p-anisaldehyde dimethyl acetal was, according to the same directives, without classification and without R phrase.

Example 5

Flash Point

Benzaldehyde dimethyl acetal has a flash point of 69° C. p-Anisaldehyde dimethyl acetal had a flash point of 114° C. (measured as specified in DIN 53213-1).

Example 6

Viscosity p-Anisaldehyde dimethyl acetal had a viscosity of 5.5 mPas at 20° C.

Example 7

Liquid Agrochemical Formulation 40 g of clodinafop-propargyl and 10 g of cloquintocet-mexyl were stirred at room temperature into a mixture of 10 g Soprophor® DSS/7 (ammonium salt of a sulfate of ethoxylated polyarylphenol, commercially available from Rhodia) in p-anisaldehyde dimethyl acetal and made up to 100 ml with p-anisaldehyde dimethyl acetal. The emulsion concentrate (EC) thus obtained shows good emulsifying behavior upon dilution (1% by weight) with standard water CIPAC-D.

Example 8

Solid Agrochemical Formulation 40 g of the emulsion concentrate of Example 7 were absorbed onto 30 g of Sipernat® 50 S (silica powder with a specific surface of 475 m²/g, mean particle size 7.5 µm). The resulting absorbate was mixed with 120 g of Perlite, 25 g of the sodium salt of a naphthalenesulfonate condensate, 5 g of Aerosol® OT-B (anionic surfactant) and 1 g of silicone-comprising antifoam. After grinding with an air jet, this mixture was made into a paste with 5% by weight of water and granulated in a laboratory extruder (bore diameter 0.8 mm). After drying, granules with good stability and with good dispersing properties are obtained.

We claim:

1. An agrochemical composition comprising a pesticide and a solvent of formula:

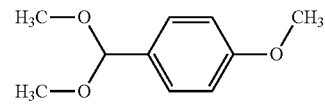

wherein the composition contains the pesticide in dissolved form;
the pesticide has a water solubility of no more than 10 g/l at 20° C.; and
the concentration of the solvent is at least 30% by weight based on the composition.

2. The composition according to claim 1, comprising at most 95% by weight of the solvent.

3. The composition according to claim 1, further comprising an anionic surfactant.

4. A process for the preparation of the composition according to claim 1, which comprises bringing the pesticide and the solvent into contact.

5. A method of controlling phytopathogenic fungi and/or undesired vegetation and/or undesired insect or mite attack and/or for regulating the growth of plants, wherein the composition according to claim 1 is applied to the respective pests, their environment or on the plants to be protected from the respective pest, on the soil and/or on undesired plants and/or on the crop plants and/or on their environment.

6. The method of claim 5, wherein the composition comprises at most 95% by weight of the solvent.

7. The method of claim 5, wherein the composition further comprises an anionic surfactant.

8. The method of claim 5, wherein the solvent has a solubility in water at 20° C. of no more than 1.0% by weight.

9. A seed treated with the composition according to claim 1.

* * * * *